US00PP08443P

United States Patent [19]

McCahon

[11] Patent Number: Plant 8,443

[45] Date of Patent: Nov. 2, 1993

[54] CHRYSANTHEMUM PLANT NAMED 'MCCAHON'S YELLOW 11-90'

[75] Inventor: Andrew McCahon, Ventura, Calif.

[73] Assignee: McCahon Floral of Carpinteria, Carpinteria, Calif.

[21] Appl. No.: 744,301

[22] Filed: Aug. 13, 1991

[51] Int. Cl.[5] ..... A01H 5/00

[52] U.S. Cl. ..... Plt./78

[58] Field of Search ..... Plt./78

[56] References Cited

U.S. PATENT DOCUMENTS

P.P. 3,231 7/1972 Jessel, Jr. et al. ..... Plt. 78

P.P. 6,801 5/1989 VandenBerg ..... Plt. 79

*Primary Examiner*—Howard J. Locker

*Attorney, Agent, or Firm*—Arnold, White & Durkee

[57] ABSTRACT

This new, medium height Chrysanthemum cultivar, designated 'McCahon's Yellow 11-90', is distinguished by its vigorous growth habit, self-branching, and yellow flowers. 'McCahon's yellow 11-90' is a color sport of the bronze flowered cultivar 'Dark Bronze Charm' (U.S. Plant Pat. No. 6,801) with all the growth characteristics which make it a desirable plant for commercial greenhouse production.

1 Drawing Sheet

BACKGROUNG OF THE INVENTION

The present invention is a new cultivar of Chrysanthemum, known as *Chrysanthemum morifolium* R. and referred to by the present inventor by the cultivar name McCahon's Yellow 11-90.

'McCahon's Yellow 11-90' is a vigorous, self-branching Chrysanthemum of medium height with clusters of yellow flowers. It has self-branching traits which make it desirable for branched plant production.

This new Chrysanthemum cultivar originated as a spontaneous mutation of the bronze flowered cultivar 'Dark Bronze Charm' in a greenhouse in Half Moon Bay, Calif. The Charm Family of Chrysanthemums include the following cultivars: Dark Bronze Charm (U.S. Plant Pat. No. 6,801), Charm (U.S. Plant Pat. No. 5,502), Coral Charm (U.S. Plant Pat. No. 7,060), Dark Charm (U.S. Plant Pat. No. 7,585), Bronze Charm (U.S. Plant Pat. No. 6,314), Salmon charm (U.S. Plant Pat. No. 6,334). The development of McCahon's Yellow 11-90' was surprising since there has never been a Yellow sport in the Charm Family of cultivars.

The following traits have been observed on McCahon's Yellow 11-90' constantly:

1—Flat capitulum form.

2—Decorative capitulum type.

3—Bright yellow ray floret color

4—Diameter across face of capitulum of up to 11 cm at maturity, when grown as a pinched disbudded pot mum.

5—Uniform eight week photoperiodic flowering response to short days.

6—Spreading branching pattern.

Of the commercial varieties grown today it is the inventors belief that the most similar to McCahon's Yellow 11-90' are Dark Bronze Charm and Sunny Mandalay (U.S. Plant Pat. No. 3,231). All traits of 'McCahon's Yellow 11-90' are similar to Dark Bronze Charm with the exception of the color of the ray florets.

This yellow sport has all the self-branching traits and other desirable growth characteristics of 'Dark Bronze Charm' which make it a desirable plant for commercial greenhouse production.

The cultivar 'McCahon's Yellow 11-90' was discovered and selected by the inventor in November of 1990 at the inventor's family nursery in Half Moon Bay, Calif. in a block of Dark Bronze Charm.

The cultivar was asexually propagated, with results of trueness showing in March, 1991. After flowering for a number of times in Half Moon Bay, the plant has shown that the characteristics herein disclosed for 'McCahon's Yellow 11-90' are firmly fixed and are retained throughout successive generations of asexual reproduction.

After selection, 'McCahon's Yellow 11-90' was vegetatively reproduced from stem cuttings for test purposes in Half Moon Bay, Calif. By subjecting clones of this plant to successive generations of vegetative propagation, it was demonstrated that the flower coloration and other distinctive characteristics of 'McCahon's Yellow 11-90' hold true from generation to generation.

DESCRIPTION OF THE PHOTOGRAPHS

Chrysanthemum cultivar 'McCahon's Yellow 11-90' is illustrated in the accompanying color photographs. The upper photo is a side view of a typical branched plant in full flower. The lower photo is a top view of the same plant showing flower formation.

DESCRIPTION OF THE PLANT

The following is a detailed description of this new Chrysanthemum observed in a greenhouse in Half Moon Bay, Calif. U.S.A. during November 1990. Recorded observations from flowering plants, grown as one pinched plant per pot were observed. The pot was 4¼ inches in diameter and 3½ inches in height. Color designations were compared to the 1986 edition of The R.H.S. Colour Chart, first published in 1966 by The Royal Horticultural Society, London, England.

THE PLANT

Origin: Sport of the cultivar 'Dark Bronze Charm'.

Classification:

*Botanic.*—*Chrysanthemum morifolium.*

*Common name.*—Chrysanthemum.

*Cultivar name.*—McCahon's Yellow 11-90'.

Form: Shrub.

Height: Medium.

Growth Habit: As a single stemmed plant, upright and vigorous. In full flower, the stem is terminated by several clusters of smaller flowering side shoots on the stem. Abundance of small flower heads make an attractive display. Observation of one plant with an overall height of 10 inches and an overall width of 5½ inches were made. The diameter of individual flowers was 2½ inches.

Branching: Branching may develop without pinching, however, branching will be enhanced by removal of the stem tip. Stem tip removal produces several branches averaging 3 to 6 with equal vigor on a single plant. The plants have a spreading branching pattern.

Growth rate: Very fast. Rooting of the stem cuttings occur in 10–12 days. The plant will flower in about eight weeks under continuous long night conditions and night temperatures of about 64 degrees F.

Foliage: The foliage is clean and uniformly green from top to bottom of the plant. The leaves are of medium size, leaves typically being about 3 inches long and 2½ inches wide.

*Leaf shape.*—Typical leaves are thick and hardy with moderate lobing. The subfoliage is lobe-shaped and serrated.

*Color.*—Upper side — darker than R.H.S. 137A. Under side — near R.H.S. 138A.

*Retention.*—The foliage retention is good even under low light intensities.

Flowers: Generally 10–15 flower heads of similar size are present when the plant is in full bloom. The flower heads are the large variety and typically about 1 inch long and 2½ inches wide.

*Shape.*—Abundance of small flower heads having slightly rounded petal tips. The flower shape appears to be nearly identical to those of the parent plant 'Dark Bronze Charm'.

*General appearance.*—Approximately 10 inches in height as a pinched pot mum with 5 to 7 long days after pinch prior to short days and 2 applications of 2500 ppm B-9.

*Flower form.*—Capitulum: Flat, decorative. Diameter: 2½ inches. Ray florets and corolla florets: Color: Bright yellow. Upper surface: yellow, slightly brighter than R.H.S. 9A. Lower surface: yellow, lighter than R.H.S. 7C.

*Reproductive organs.*—Androecium: Present on disc florets, only few; scant pollen. Gynoecium: Present on both Ray and Corolla disc florets.

*Color.*—Upper side — yellow, slightly brighter than R.H.S. 9A. Under side — yellow, lighter than R.H.S. 7C.

What is claimed is:

1. A new and distinct Chrysanthemum cultivar, substantially as herein shown and described, distinguished by its vigorous growth habit, self-branching characteristics, and several bright yellow ray florets.

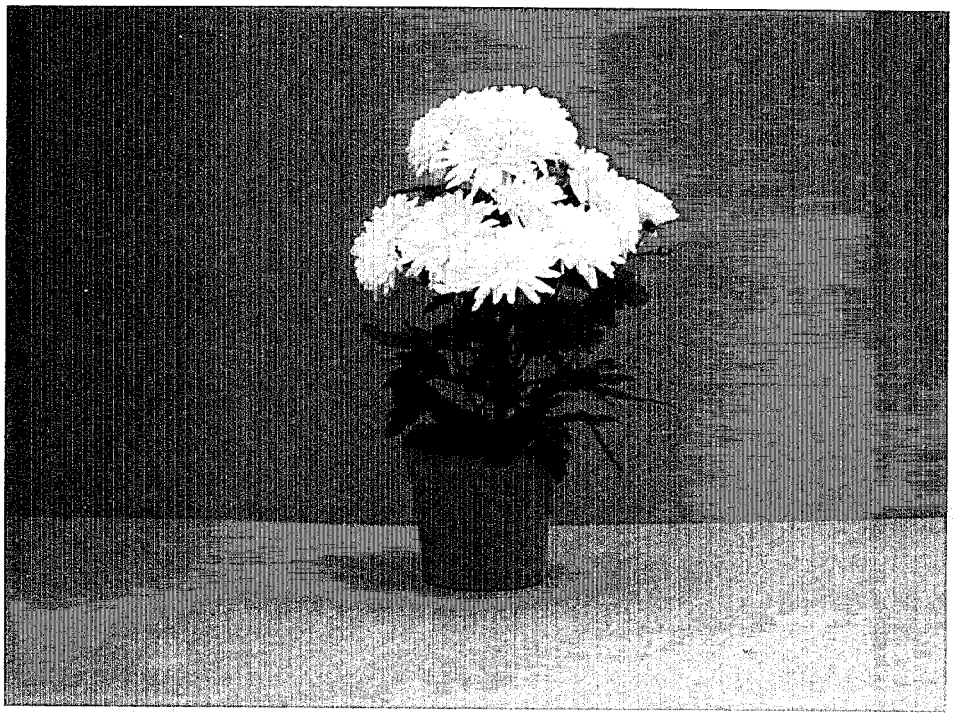
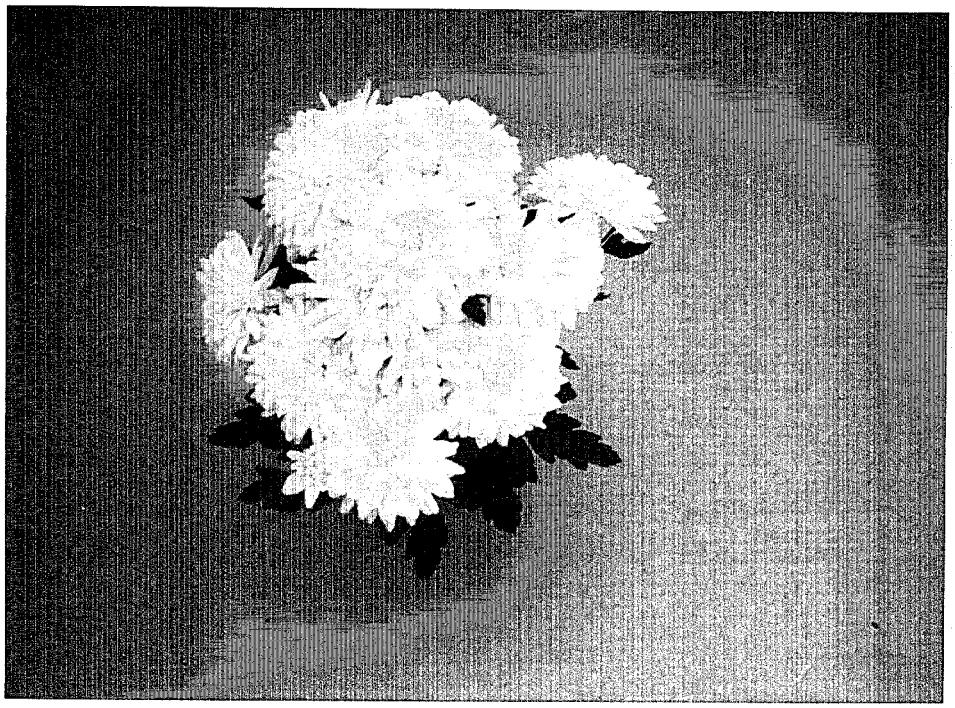

* * * * *